United States Patent
Bleam et al.

[11] Patent Number: 6,143,016
[45] Date of Patent: Nov. 7, 2000

[54] SHEATH AND METHOD OF USE FOR A STENT DELIVERY SYSTEM

[75] Inventors: Jefferey C. Bleam, Boulder Creek; Andrew J. MacKenzie, Santa Clara, both of Calif.

[73] Assignee: Advanced Cardiovascular Systems, Inc., Santa Clara, Calif.

[21] Appl. No.: 08/840,487

[22] Filed: Apr. 21, 1997

[51] Int. Cl.[7] .................................................. A61M 29/00
[52] U.S. Cl. ........................ 606/198; 606/194; 604/104
[58] Field of Search ................................. 606/159, 191, 606/194, 195, 198; 604/53, 104; 623/1, 11, 12

[56] References Cited

U.S. PATENT DOCUMENTS

| | | |
|---|---|---|
| 3,657,744 | 4/1972 | Ersek . |
| 4,569,347 | 2/1986 | Frisbie ..................................... 606/108 |
| 4,580,568 | 4/1986 | Gianturco . |
| 4,733,665 | 3/1988 | Palmaz . |
| 4,763,654 | 8/1988 | Jang . |
| 4,921,484 | 5/1990 | Hillstead ................................ 604/104 |
| 5,002,532 | 3/1991 | Gaiser et al. . |
| 5,061,273 | 10/1991 | Yock . |
| 5,102,417 | 4/1992 | Palmaz . |
| 5,195,984 | 3/1993 | Schatz . |
| 5,226,889 | 7/1993 | Sheiban . |
| 5,454,790 | 10/1995 | Dubrul ..................................... 604/104 |
| 5,456,694 | 10/1995 | Marin et al. . |
| 5,569,296 | 10/1996 | Marin et al. . |
| 5,571,086 | 11/1996 | Kaplan . |
| 5,634,928 | 6/1997 | Fischell et al. . |
| 5,643,278 | 7/1997 | Wijay . |
| 5,647,857 | 7/1997 | Anderson et al. . |
| 5,649,906 | 7/1997 | Gory et al. ............................... 604/53 |
| 5,709,701 | 1/1998 | Parodi ..................................... 606/194 |
| 5,735,869 | 4/1998 | Fernandez-Aceytuno ............... 606/194 |

FOREIGN PATENT DOCUMENTS

| | | |
|---|---|---|
| 0 274 846 | 7/1988 | European Pat. Off. . |
| 0 479 557 | 4/1992 | European Pat. Off. . |
| 0 505 686 | 9/1992 | European Pat. Off. . |
| 0 540 290 A2 | 5/1993 | European Pat. Off. . |
| 0 621 017 | 10/1994 | European Pat. Off. . |
| 0 637 431 | 2/1995 | European Pat. Off. . |
| 0 732 087 A1 | 9/1996 | European Pat. Off. . |
| 6-181993 | 7/1994 | Japan . |
| WO 96/33677 | 10/1996 | WIPO . |
| WO 96/39077 | 12/1996 | WIPO . |
| WO 97/09932 | 3/1997 | WIPO . |

*Primary Examiner*—Michael Buiz
*Assistant Examiner*—Vy Quang Bui
*Attorney, Agent, or Firm*—Fulwider Patton Lee & Utecht, LLP

[57] ABSTRACT

An apparatus and method for deploying one or more stents within a body lumen comprises a substantially tubular sheath configured for slidable movement over a catheter shaft and configured to receive a stent over a flexible, expandable distal portion of the sheath. The sheath may comprise a part of a stent deployment system including a dilatation catheter (such as a balloon catheter), and one or more substantially tubular stents positioned in their delivery configurations over the expandable distal portion of the sheath. The sheath preferably has a proximal portion that is configured so that a user may advance the sheath over the catheter by maneuvering the sheath proximal end. The substantially tubular stent is preferably a radially expandable stent having a delivery configuration and a deployed configuration.

When the apparatus is introduced into a body lumen, the sheath is positioned on the catheter shaft such that the sheath distal portion bearing the stent is proximal of the catheter expandable member (e.g., balloon). Thus, the catheter expandable member may be used to dilate the body lumen without deploying the stent. After dilatation is completed, the sheath is advanced until the stent is positioned around the expandable member which is then expanded, thereby radially expanding and deploying the stent or stents.

34 Claims, 8 Drawing Sheets

SHEATH AND METHOD OF USE FOR A STENT DELIVERY SYSTEM

BACKGROUND OF THE INVENTION

1. Field of the Invention

The invention relates to stent delivery systems, which are used to implant a stent into a patient's body lumen to maintain the patency thereof. More particularly, the present invention relates to a stent delivery sheath that is mounted over a catheter for deploying a stent in a body lumen.

2. Description of Related Art

Stents are generally cylindrically-shaped devices which function to hold open and sometimes expand a segment of a blood vessel or other body lumen. They are particularly suitable for use to support and hold back a dissected arterial lining which can occlude the fluid passageway. Stents also are useful in maintaining the patency of a body lumen, such as a coronary artery, after a percutaneous transluminal coronary angioplasty (PTCA) procedure or an atherectomy procedure to open a stenosed area of the artery. Several interventional treatment modalities are presently used for heart disease, including balloon and laser angioplasty, atherectomy, and bypass surgery.

In typical balloon angioplasty procedures, a guiding catheter having a preformed distal tip is percutaneously introduced through the femoral artery into the cardiovascular system of a patient in a conventional Seldinger technique and advanced within the cardiovascular system until the distal tip of the guiding catheter is seated in the ostium of a desired coronary artery. A guidewire is positioned within an inner lumen of a dilatation catheter, and then both are advanced through the guiding catheter to the distal end thereof. The guidewire is advanced out of the distal end of the guiding catheter into the patient's coronary vasculature until the distal end of the guidewire crosses a lesion to be dilated. Then, the dilatation catheter, having an inflatable balloon on the distal portion thereof, is advanced into the patient's coronary anatomy over the previously-introduced guidewire until the balloon of the dilation catheter is properly positioned across the lesion. Once in position across the lesion, the balloon, which is typically made of relatively non-distensible materials, is inflated to a predetermined size with liquid at relatively high pressure (e.g., greater than 4 atmospheres) to compress the arteriosclerotic plaque of the lesion against the inside of the artery wall and to otherwise expand the inner lumen of the artery. The dilatation balloon is then deflated so that blood flow can be resumed through the dilated artery and the dilatation catheter can be removed. Further details of dilatation catheters, guidewires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson et al.); U.S. Pat. No. 4,554,929 (Samson et al.); U.S. Pat. No. 4,616,652 (Simpson); U.S. Pat. No. 4,638,805 (Powell); U.S. Pat. No. 4,748,982 (Horzewski et al.); U.S. Pat. No. 5,180,368 (Garrison); U.S. Pat. No. 5,458,613 (Gharibadeh et al.); and U.S. Pat. No. 5,496,346 (Horzewski et al.), which are hereby incorporated herein in their entirety by reference thereto.

A major problem that can occur during balloon angioplasty procedures is the formation of intimal flaps that can collapse and occlude the artery when the balloon is deflated at the end of the angioplasty procedure. Another major problem characteristic of balloon angioplasty procedures is the large number of patients which are subject to restenosis in the treated artery. In the case of restenosis, the treated artery may again be subject to balloon angioplasty or to other treatments such as bypass surgery, if additional balloon angioplasty procedures are not warranted. However, in the event of a partial or total occlusion of an artery resulting from the collapse of a dissected arterial lining after the dilatation balloon is deflated, the patient may require immediate medical attention, particularly where the occlusion occurs in a coronary artery.

A major focus of recent development work in the treatment of heart disease has been directed to endoprosthetic devices called stents. Stents are generally cylindrically-shaped intravascular devices that are placed within a damaged artery to hold it open. Such devices can be used to reduce the development of restenosis or to tack up an intimal flap to maintain the patency of the blood vessel immediately after intravascular treatments such as a PTCA.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition, and then deflating the balloon and removing the catheter.

However, the rapid and effective delivery of a stent to the desired location within a patient's vasculature is difficult and time consuming, particularly where stent deployment is accompanied by a balloon angioplasty procedure or where multiple stents are deployed in the body lumen.

It may therefore be important to improve existing stent delivery systems to provide rapid stent delivery while at the same time allowing a surgeon to select a desired stent and catheter combination. The present invention satisfies these needs.

SUMMARY OF THE INVENTION

The present invention is directed to an apparatus and method for deploying one or more stents within a body lumen. The invention generally comprises a substantially tubular sheath configured for slidable movement over a catheter shaft, with the sheath configured to have a substantially tubular stent positioned over a distal portion of the sheath. The sheath may comprise a part of a stent deployment system including a substantially tubular stent positioned over a distal portion of the sheath and a catheter slidably received within the sheath.

The substantially tubular sheath preferably has proximal and distal ends, proximal and distal portions, an outer surface, and a lumen therethrough defining an inner surface. The sheath is configured for slidable movement over the catheter shaft. The distal portion of the sheath comprises a flexible, expandable material extending from the inner surface of the sheath to the outer surface of the sheath. The proximal portion of the sheath is resistant to compressive forces.

The catheter is preferably a dilatation catheter or a balloon catheter having an expandable member, such as a balloon, at its distal end. The substantially tubular stent is preferably a radially expandable stent having a delivery configuration and a deployed configuration. The stent is positioned in the delivery configuration over the distal portion of the sheath.

When the apparatus is introduced into a body lumen, the sheath is positioned on the catheter shaft such that the sheath distal portion bearing the stent is proximal of the expandable member. Accordingly, the expandable member may be freely expanded, in the body lumen, as may be necessary to dilate a selected portion of the body lumen, without radially expanding, and thereby deploying, the stent. Once the body lumen has been dilated by the expandable member, the sheath can be longitudinally advanced until the sheath distal portion bearing the stent is positioned over the expandable member. The expandable member can then be expanded. Because the sheath distal portion is formed of an elastomeric material, the sheath distal portion expands as the expandable member expands. This expansion of the expandable member and sheath distal portion also expands and deploys the stent at the desired location. The expandable member can then be deflated, thereby causing the sheath distal portion to resume its unexpanded form. The stent retains its deployed, expanded form, and remains in the body lumen as the catheter and sheath are withdrawn.

In an alternative embodiment, all or part of the proximal portion of the tubular sheath is replaced by a stiff mandrel sized and configured to lay along the side of the catheter shaft. The mandrel may be of either a solid or hollow configuration. Such an embodiment may be used with so-called rapid exchange catheters such as the catheters shown and described in U.S. Pat. No. 5,180,368 (Garrison), U.S. Pat. No. 5,458,613 (Gharibadeh et al.), and U.S. Pat. No. 5,496,346 (Horzewski et al.).

In one embodiment, the proximal portions of the catheter and sheath have positioning indicia, such as visible markings or surface disruptions, on their proximal portions, that may be viewed by a user during a procedure. The positioning indicia can be used to indicate the relative position of the stent with respect to the expandable member. By aligning the positioning indicia of the sheath and catheter, the user can determine when the stent is positioned over the expandable member. The proximal portion of the sheath may also contain indicia that describe features of the apparatus, such as the length of the sheath and the number and type of stents secured to the sheath.

The tubular sheath proximal portion preferably has a length of at least 50 cm, depending on the particular application and body lumen to be treated. The length of the proximal portion should be sufficient to allow the proximal end of the sheath to be outside of the patient while the distal portion that bears the stent is at the desired deployment site inside the body lumen. The tubular sheath proximal portion is preferably resistant to compressive forces, so that a user may advance the sheath along the catheter by grasping the proximal end of the sheath and pushing the sheath distally.

The invention can be used with various catheters, including so-called over-the-wire catheters and rapid exchange catheters.

The sheath may contain one or more stents. Where two or more stents are mounted on the sheath, the apparatus can be used to deploy multiple stents in the body lumen without requiring the catheter or sheath to be withdrawn from the body lumen until deployment of all stents is completed.

The sheath distal portion protects the expandable member, such as a dilatation balloon, from mechanical damage that might otherwise be caused by the stent or by characteristics of the lesion itself. The distal portion also aids in deflating and refolding the balloon after stent deployment, as well as offering some protection to the body lumen against damage from rupture of the balloon.

The delivery sheath of the invention is of particular use with a catheter having a removable proximal hub, such as that described in co-pending application Ser. No. 08/840, 495, now U.S. Pat. No. 6,019,777, issued Feb. 1, 2000, for CATHETER AND METHOD FOR A STENT DELIVERY SYSTEM, with Andrew James Mackenzie as the inventor, filed concurrently herewith and incorporated herein by reference.

Other features and advantages of the present invention will become more apparent from the following detailed description of the invention when taken in conjunction with the accompanying drawings.

DETAILED DESCRIPTION OF THE PREFERRED EMBODIMENTS

The present invention is depicted in FIGS. 1–15 for use in various body lumens and procedures, including use in deploying stents in dilated arteries during balloon angioplasties. However, the present invention is not limited to use in blood vessels or angioplasties, but can be used in other body lumens and procedures to deploy stents, endovascular grafts, and similar devices.

Figure 1:
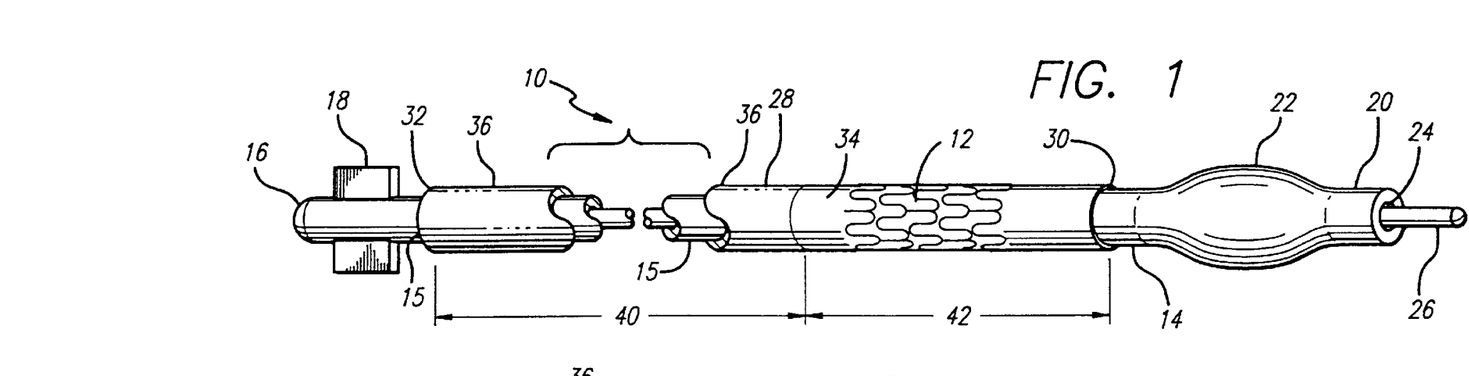
FIG. 1 is a perspective view, partially in section, depicting a delivery catheter, sheath, and stent assembly according to the present invention.

Referring to FIG. 1, in one preferred embodiment the assembly 10 for deploying stent 12 includes a balloon catheter 14. The balloon catheter 14 has a catheter shaft 15, a proximal end 16 with various controls 18 located thereon, and a distal end 20 having a dilatation device, which in the embodiment shown is a dilatation balloon 22. Although it is preferred that balloon 22 be a dilatation balloon, the device is not so limited, and can include any expandable member capable of expanding a stent. In the embodiment shown, the balloon catheter 14 has an inner lumen 24 that allows a guidewire 26 to pass therethrough.

The assembly 10 further includes a sheath 28 having a distal end 30 and a proximal end 32. The sheath 28, which is shown in greater detail in FIG. 2, comprises two portions—a distal portion 34 and a proximal portion 36. The distal portion 34 preferably comprises an elastic, expandable material that can be expanded by outward pressure from within the sheath 28. Such materials as elastomeric polymers and urethane, rubber, latex and Tecoflex® may be used to form the distal portion 34. The proximal portion 36 is preferably formed of a material, such as PEEK (polyether ether keytone), a stiff plastic such as ABS (acrylonitrile-butadiane-styrene) or PVC (polyvynle chloride), a flexible metal tube formed from stainless steel or nitinol (NiTi) alloys, or a fiber or braid reinforced tube from any combination of these materials, all of which enhance the pushability of sheath 28 yet is flexible enough to navigate the vascular system. The proximal portion length 40 is typically several times the distal portion length 42.

Figures 2, 3A, 3B:
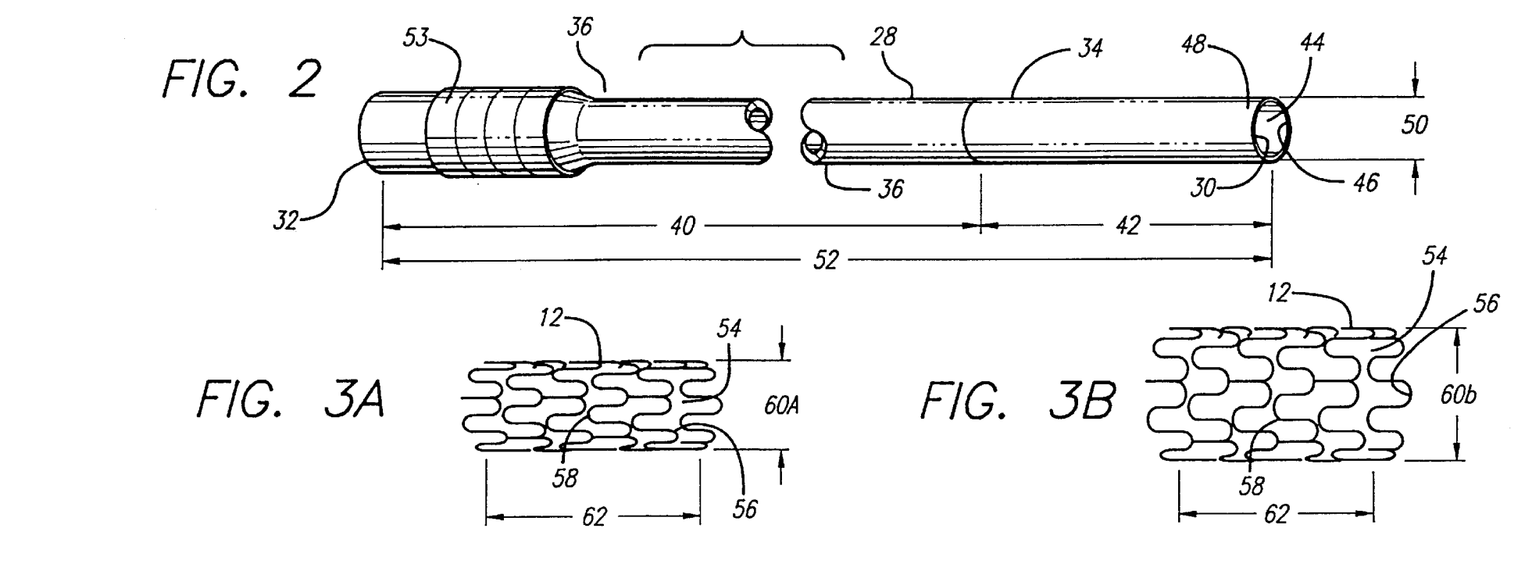
FIG. 2 is a perspective view of a sheath according to the present invention.
FIG. 3a is a perspective view of a stent in a delivery configuration.
FIG. 3b is a perspective view of the stent of FIG. 3a in a deployed configuration.

The sheath 28 shown in FIG. 2 has an inner lumen 44 passing along the length of the sheath 28. The sheath has an inner surface 46, defined by the inner lumen 44, and an outer surface 48. The inner lumen 44 is sized for slidable movement over dilatation balloon catheter 14 and particularly catheter shaft 15.

The sheath 28 of FIG. 2 has an outer diameter 50 sized to pass within a body lumen. The sheath 28 preferably has a length 52 that allows the sheath distal end 30 to be positioned at a desired treatment site in a body lumen while the sheath proximal end 32 is positioned outside of the body lumen and patient, so that a user can manipulate the sheath 28 by grasping and maneuvering the sheath proximal end 32. Maneuvering the proximal end 32 of sheath 28 provides relative axial movement between the sheath distal end 30 and the dilatation balloon 22 so that the stent 12 is thereby positioned at the desired treatment site. The proximal portion 36 may include a handle 53 or similar manipulation device by which a user can grasp and move the sheath 28 axially over catheter shaft 15.

Figure 5:
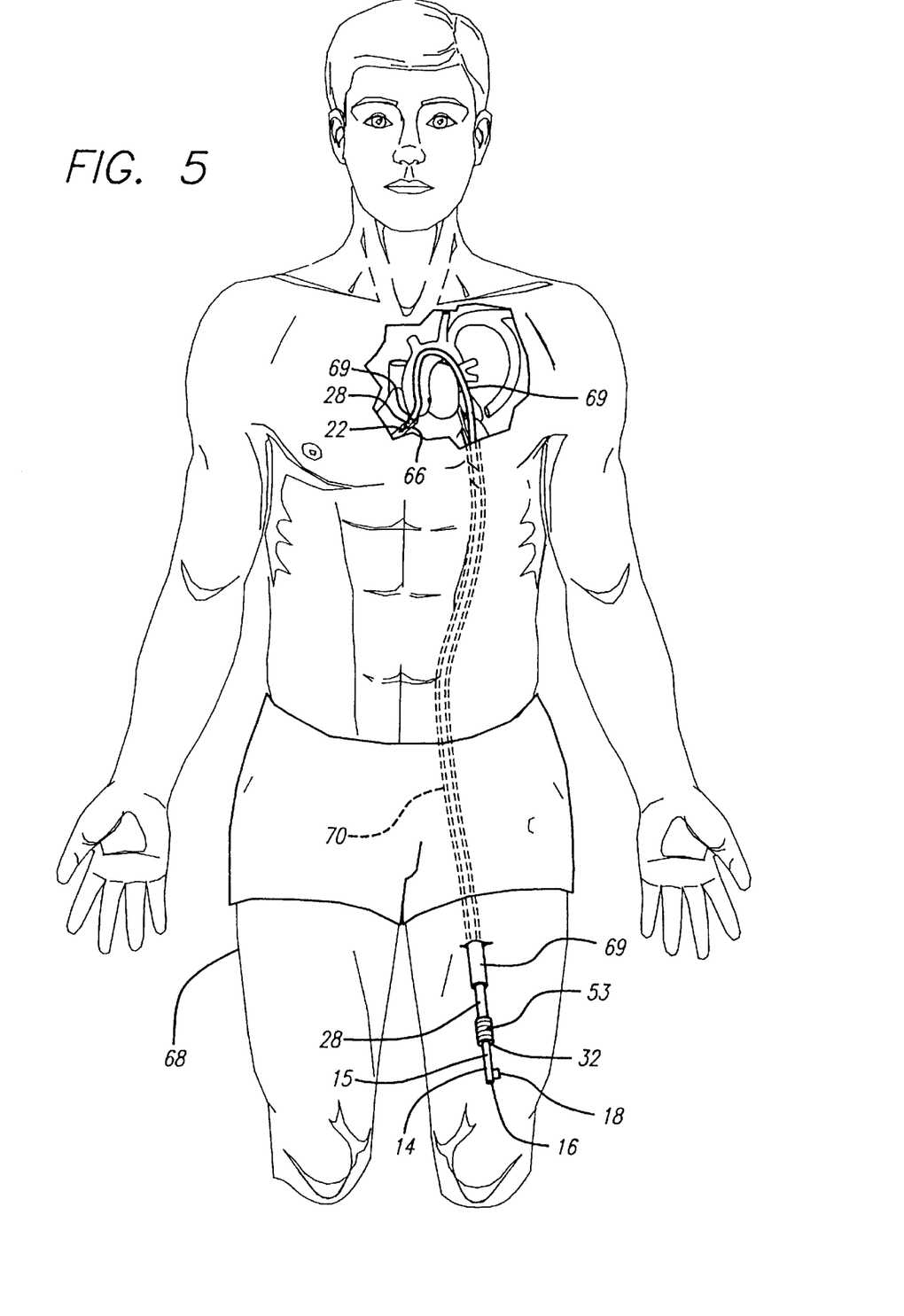
FIG. 5 is a perspective view, partially in section, of a delivery catheter and sheath assembly used to deploy a stent in a human patient according to the present invention.

Different sheaths can have various lengths, depending on the particular application. For example, in a balloon angioplasty procedure where a sheath is used to deploy a stent in a coronary artery (as shown in FIG. 5), the sheath length 52 is generally at least 50 cm in length, and will preferably be on the order of 100 cm to 140 cm in length. The precise length will be determined by the application.

FIGS. 3a and 3b show an expandable stent 12 for use with the balloon catheter 14 and sheath 28 of the current invention. The stent has an inner lumen 54 defining an inner surface 56, and an outer surface 58 defining an outer diameter 60a. FIG. 3a shows the stent 12 in its delivery configuration, whereby the outer diameter 60a is small enough to pass within a body lumen. FIG. 3b shows the stent 12 in its deployed configuration, whereby the outer diameter 60b is sized so that the stent outer surface 58 contacts the walls of the body lumen. The length 62 of the stent 12 is typically in the range of 5 to 50 mm, and preferably about 15 to 20 mm, but stents of almost any length may be used with the invention, depending on the particular application. FIGS. 3a and 3b show a stent 12 of an open lattice configuration, similar to the stent described in co-pending and commonly owned U.S. Ser. No. 08/454,599, which is incorporated herein by reference. However, other stent types and configurations are well known in the art and also are compatible with the invention, so long as the stent defines an inner lumen and can be partially or fully expanded with a device such as a balloon catheter.

Figure 4:
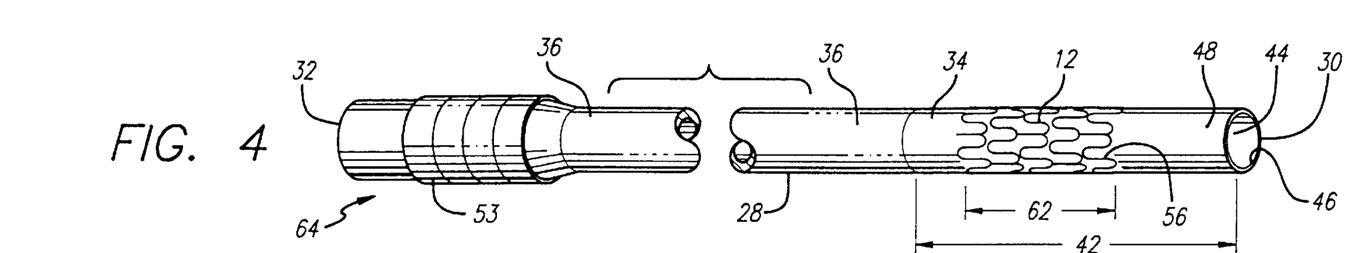
FIG. 4 is a perspective view of a sheath and stent assembly according to the present invention.

FIG. 4 shows a stent and sheath assembly 64 according to a preferred embodiment of the current invention. The stent 12 is positioned in its delivery configuration on the sheath distal portion 34, with the stent inner surface 56 contacting the sheath outer surface 48. In the preferred embodiment shown, the sheath distal portion length 42 is greater than the stent length 62, so that the stent 12 can be mounted entirely on the sheath distal portion 34 without contacting the sheath proximal portion 36.

In one embodiment of the invention, one or more stents 12 are preloaded onto the sheath distal portion 34 at the point of manufacture. Accordingly, the user does not have to manually load the stent onto the sheath distal portion 34, and instead selects a sheath distal portion 34 that has a desired stent 12 or stents preloaded thereon. In an alternative embodiment, the stent 12 is not preloaded onto the sheath distal portion 34 at the point of manufacture. Instead, the user selects a desired stent(s) 12, and loads the stent 12 onto the sheath distal portion 34.

Figure 4A:
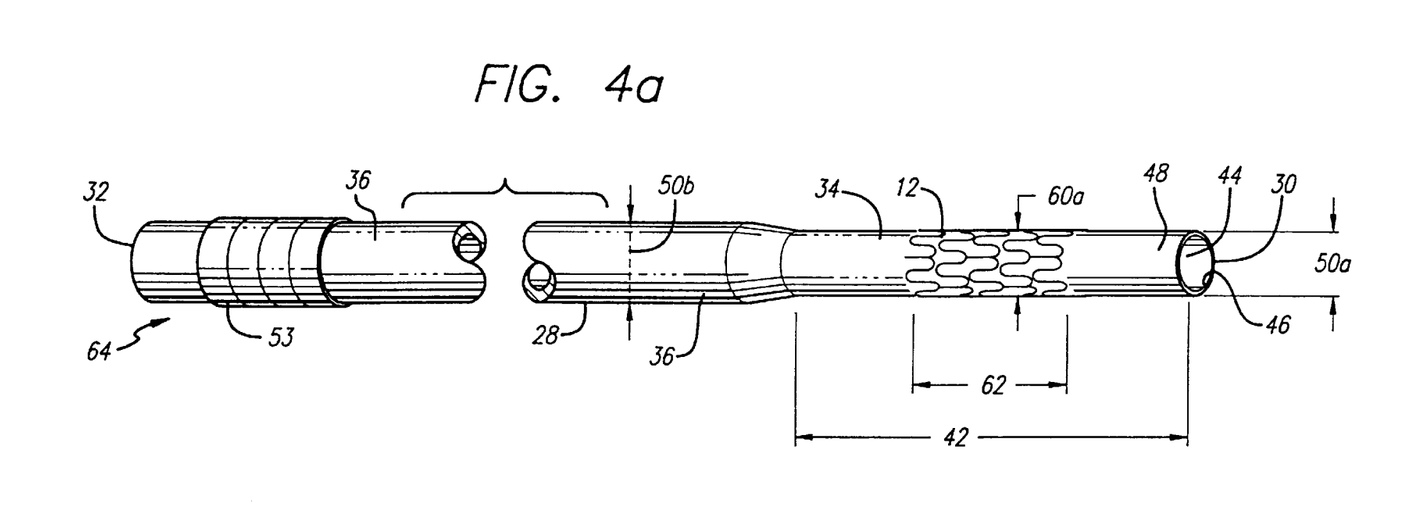
FIG. 4a is a perspective view of an alternative embodiment of a sheath and stent assembly according to the present invention.

In the embodiment shown in FIGS. 2 and 4, the sheath distal portion 34 and the sheath proximal portion 36 have the same diameter 50. However, in other embodiments the diameter of the distal portion 34 and the proximal portion 36 may vary. For example, as depicted in FIG. 4a, the sheath distal portion 34 may have a diameter 50a slightly smaller than the diameter 50b of the sheath proximal portion 36. The reduced diameter 50a of the sheath distal portion 34 allows extra radial space for a stent 12 to be positioned on the sheath 28, so that the outer diameter 60a of the stent 12 when mounted on the sheath distal portion 34 in delivery configuration can easily pass within a body lumen. In one embodiment, such as that shown in FIG. 4a, the outer diameter 60 of the stent 12 is equal to or less than the diameter 50b of the sheath proximal portion 36.

In FIG. 5, the catheter, sheath, and stent assembly are used in a balloon angioplasty procedure to deploy a stent 12 in a coronary artery 66 in a patient 68. The assembly has been percutaneously introduced through a guide catheter 69 in the femoral artery 70 into the vascular system of the patient 68, with the dilatation balloon 22 positioned, for example, in the coronary artery to be treated. Both the catheter proximal end 16, which includes the catheter controls 18, and the sheath proximal end 32, including the sheath handle 53, are positioned outside of the patient 68 so that a user may easily grasp and manipulate the catheter 14 and sheath 28.

Figure 6:
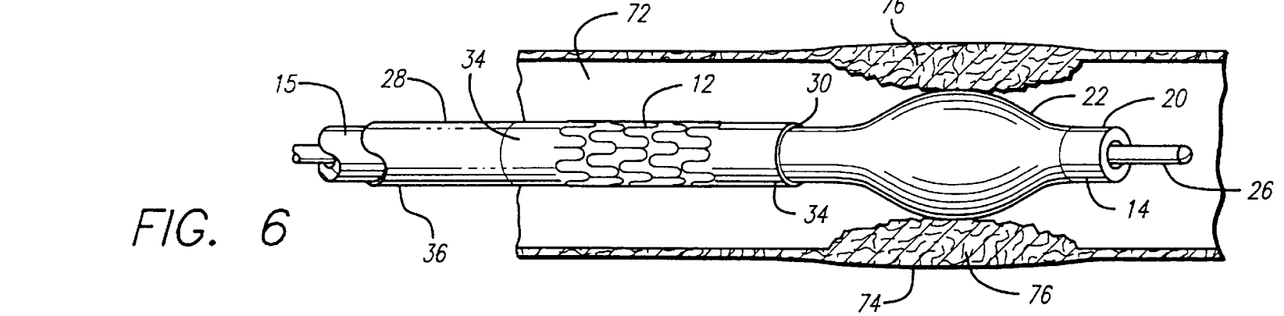
FIG. 6 is a perspective view of a distal portion of a delivery catheter, sheath, and stent assembly with the balloon expanded to dilate a body lumen.

Referring now to FIG. 6, the catheter/sheath/stent assembly is shown with the dilatation balloon 22 positioned within a body lumen 72 at a desired treatment location 74. The desired treatment location 74 may comprise blockage 76, such as a stenosis caused by deposits of plaque, that partially occludes the body lumen 72.

Figure 6A:
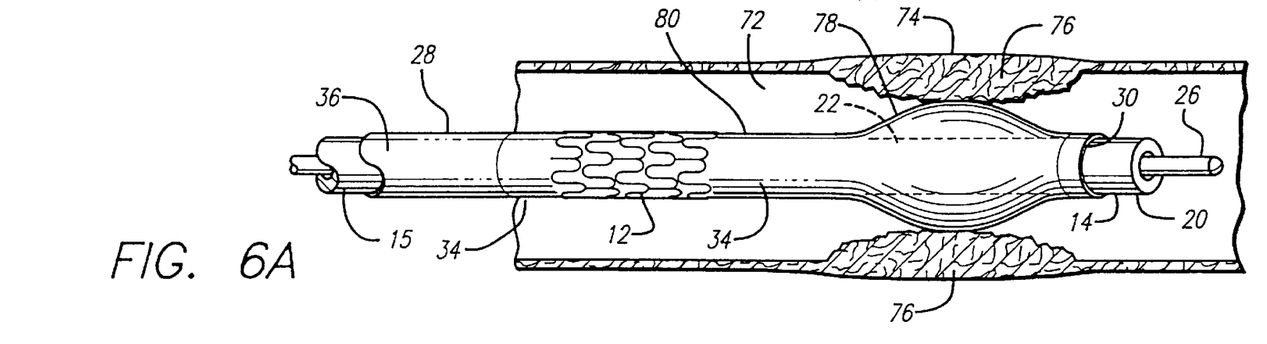
FIG. 6a is a perspective view of a distal portion of an alternative embodiment of a delivery catheter, sheath, and stent assembly with the balloon expanded to dilate a body lumen.

The sheath 28 is positioned such that the stent 12, which is mounted on the sheath distal portion 34, is just proximal of the dilatation balloon 22. Accordingly, as the dilatation balloon 22 is expanded against the blockage 76, the expansion of the dilatation balloon 22 does not cause the stent 12 to assume its deployed diameter. In the embodiment shown in FIG. 6, the sheath distal end 30 is positioned just proximal of the dilatation balloon 22, so that expansion of the dilatation balloon 22 does not cause expansion of any part of the sheath distal portion 34. However, in another embodiment, as shown in FIG. 6a, the sheath 28 may have a sheath distal portion 34 significantly longer than the stent 12, with the sheath distal portion 34 extending distally of the stent 12 and over the dilatation balloon 22. In such an embodiment, the expansion of the dilatation balloon 22 to dilate the blockage 76 will expand a forward section 78 of the sheath proximal portion 34, but the rear section 80 of the sheath proximal portion 34, upon which the stent 12 is mounted, is not significantly expanded, so that the expansion of the dilatation balloon 22 to treat the blockage 76 does not cause the stent 12 to assume its deployed diameter.

Figures 7, 8:
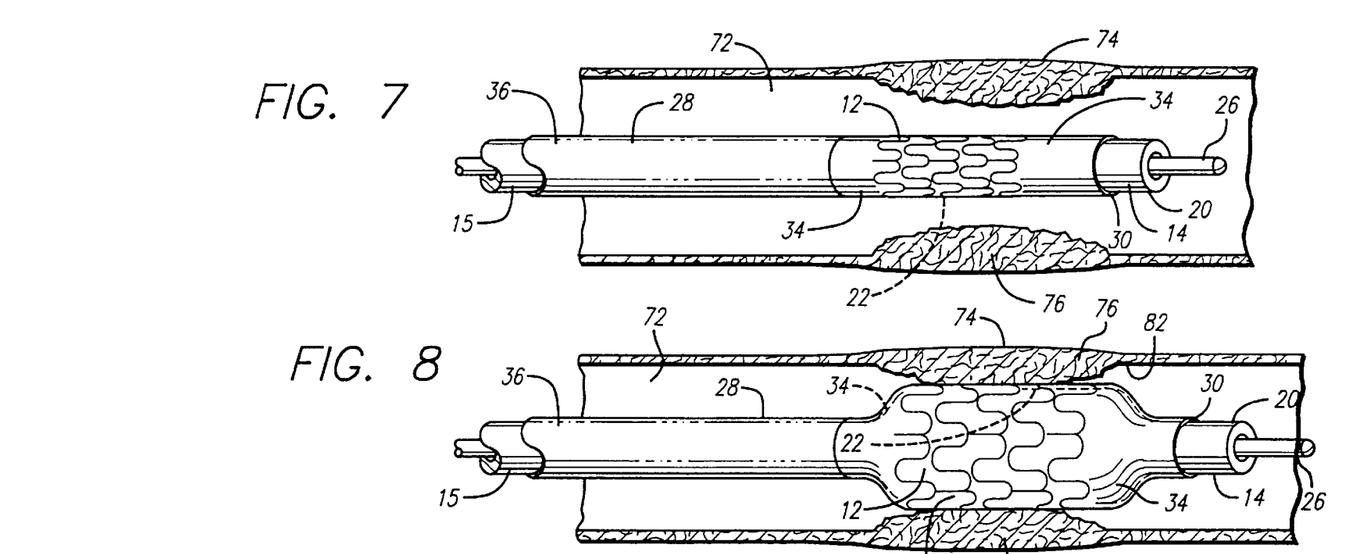
FIG. 7 is a perspective view depicting the distal portion of the delivery catheter, sheath, and stent assembly of FIG. 6 with the stent positioned for deployment in the body lumen.
FIG. 8 is a perspective view depicting the distal portion of the delivery catheter, sheath, and stent assembly of FIG. 6 with the balloon expanded to deploy the stent in the body lumen.

In FIG. 7, the blockage 76 has been dilated and the dilatation balloon 22 has been deflated. The sheath 28 has been slidably advanced (distally) over the catheter 14 by maneuvering the sheath proximal end 32 until the stent 12 is positioned over the dilatation balloon 22. The slidable advancement of the sheath 28 may be achieved by the user, such as a cardiologist, grasping the sheath proximal end 32, shown in FIG. 5, and pushing the sheath 28 forward (distally) along the catheter 14. Because the sheath proximal portion 36 preferably consists of a generally stiffer material that is resistant to longitudinal compressive forces, the user pushing on the sheath proximal end 32 causes the sheath 28 to slide over the catheter 14 so that the distal portion of the sheath 34, including the stent 12, advances over the dilatation balloon 22.

In FIG. 8, the dilatation balloon 22 is expanded. The outward pressure from the dilatation balloon 22 causes the sheath proximal portion 36 to expand outwardly, which in turn forces the stent 12 to expand outwardly until the stent assumes its deployed outer diameter 60b. In the deployed diameter, the stent outer surface 58 contacts and exerts some outward pressure against the walls 82 of the body lumen 72, thereby preventing the walls 82, which may be weakened from the dilatation procedure, or the blockage 76, from collapsing inwardly and causing renewed blockage of the body lumen 72.

Figure 9:
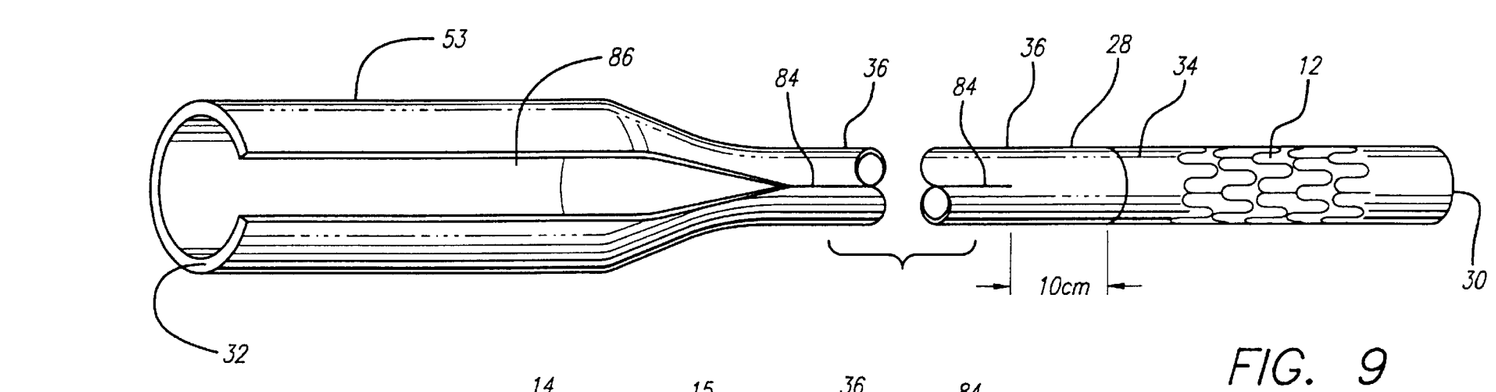
FIG. 9 is a perspective view depicting an alternative embodiment of the sheath.

FIG. 9 shows another embodiment of a sheath 28 according to the current invention. The sheath 28 is similar to that shown in FIG. 2, and comprises a distal end 30, a proximal end 32, a distal portion 34, and a proximal portion 36. However, the embodiment shown in FIG. 9 further includes a slit 84 extending from the sheath proximal end 32 toward the sheath distal end 30. The slit 84 preferably passes all the way through the sheath outer wall, i.e., from the sheath outer surface through to the sheath inner surface, and allows the sheath to be peeled apart to allow introduction or removal of various devices, such as a catheter or guidewire, via the side of the sheath. Because an opening in the side of the expandable distal portion 34 could complicate expansion and contraction of the distal portion 34, the slit 84 preferably terminates proximal of the sheath expandable distal portion 34. In the embodiment shown, the slit 84 terminates approximately 10 cm proximal of the distal portion 34 of the sheath 28.

In the embodiment shown in FIG. 9, the sheath 28 has a handle 53 by which a user may grasp and manipulate the sheath. The handle 53 includes a slot 86 sized to accommodate a catheter shaft, so that a catheter shaft and/or a guidewire may pass therethrough.

Figure 10:
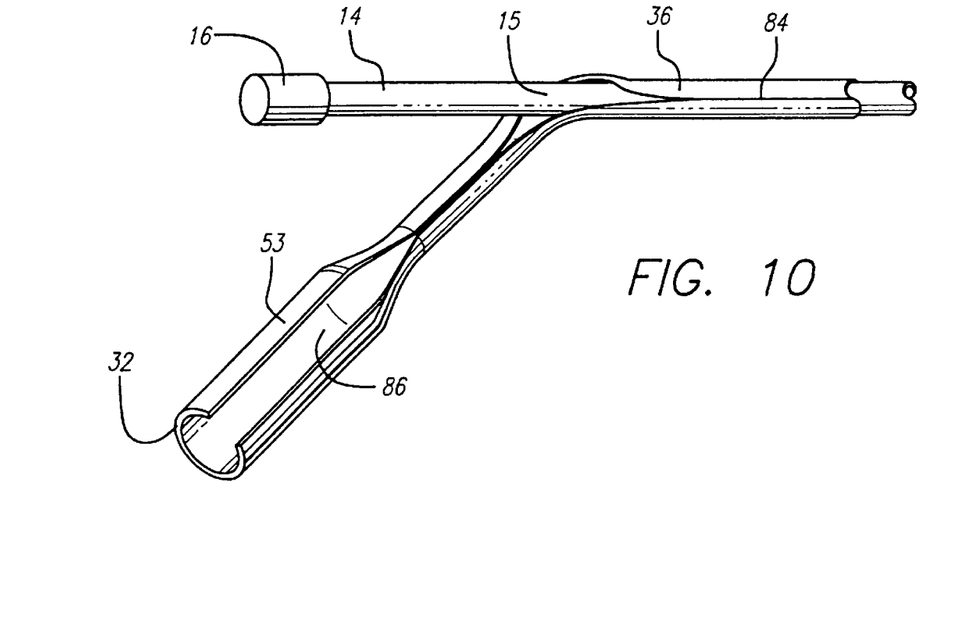
FIG. 10 is a perspective view of the sheath of FIG. 9 being removed from a catheter.

The slit 84 and slot 86 facilitate removal of the sheath 28 from a catheter 14 by allowing the sheath to be peeled away from the catheter as the sheath is withdrawn from the patient. As depicted in FIG. 10, as the sheath 28 is withdrawn, the user can peel the sheath 28 away from the catheter 14, starting from the sheath proximal end 32. Thus, a user can peel the sheath 28 away from the catheter 14 while securely holding the catheter proximal end 16. When the sheath 28 has been entirely removed from the patient, the only portions of the sheath 28 that still remain on the catheter 14 are the sheath distal portion 34 and the "unslit" portion of the sheath proximal portion 36 (such as the last 10 cm depicted in FIGS. 9 and 10). Removal of the sheath 28 can be completed by slitting the sides of the sheath distal portion 34 and the (previously) unslit portion of the sheath proximal portion 36. Alternatively, the sheath distal portion 34 and remaining unslit part of the sheath proximal portion 36 may be slid off the catheter proximal portion 16, especially where the catheter proximal portion 16 has a sufficiently small diameter to pass through the sheath distal portion 34 and the short pushable section 92, or where the catheter 14 is equipped with a detachable proximal hub such as that described in patent application Ser. No. 08/840,495, now U.S. Pat. No. 6,019,777, issued Feb. 1, 2000, entitled CATHETER AND METHOD FOR A STENT DELIVERY SYSTEM, filed concurrently herewith.

Figure 11:
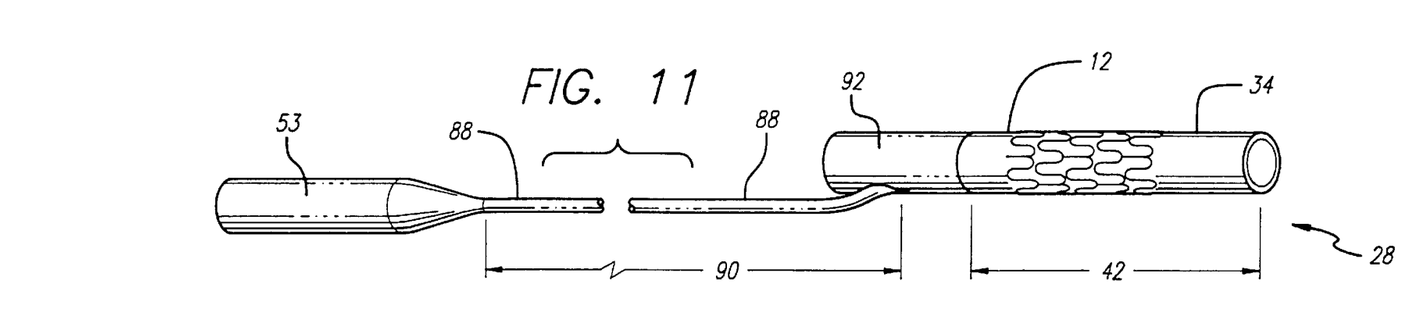
FIG. 11 is a perspective view of an alternative embodiment of a sheath and stent assembly according to the present invention.

FIG. 11 shows an alternative embodiment of a delivery sheath 28 having a distal portion 34 to which a stent 12 is secured, but wherein most of the proximal portion is replaced by a mandrel 88. The mandrel 88 performs much as the proximal portion 36 described above with respect to FIG. 2. The mandrel 88 is preferably formed of a material, such as a semi-rigid polymer, stainless steel, titanium, nickel-titanium, or similar materials, which enhances the pushability of the sheath 28 yet is flexible enough to navigate the vascular system. The mandrel 88 may have a cross-section selected from various configurations, such as solid, hollow, tubular, etc. The mandrel length 90 is typically several times the length 42 of the distal portion 34. While the sheath proximal portion 36 shown in FIG. 2 is configured to slidably pass over a catheter, the mandrel 88 of FIG. 11 is configured to pass and lie alongside a catheter. The mandrel 88 may include a handle 53 by which a user can grasp the device.

A short section of pushable sheath 92, of similar material and characteristics to the proximal portion 36 of the embodiment shown in FIG. 2, may be provided to facilitate the transition between the stiff mandrel 88 and the expandable sheath distal portion 34. This short pushable section 92 aids the pushability and trackability of the sheath 28, and prevents tearing that might result if the mandrel 88 were secured directly to the expandable sheath distal portion 34.

Figures 12, 12A:
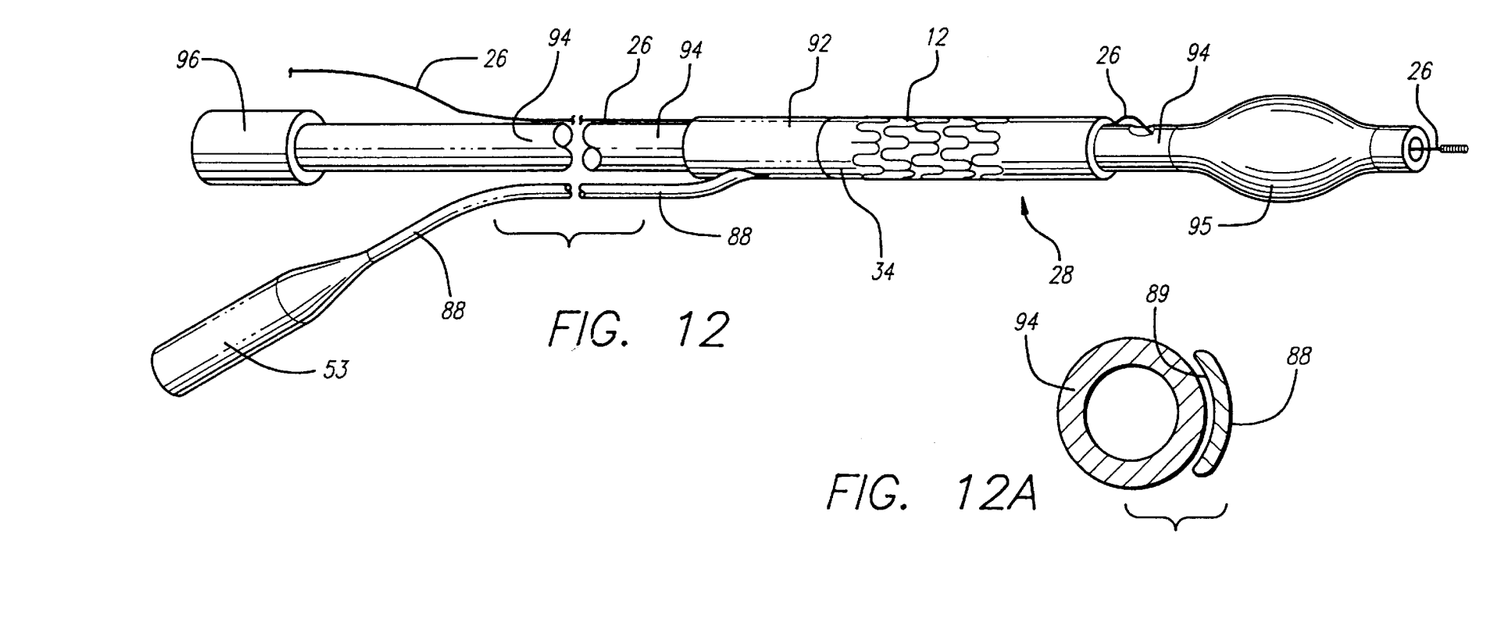
FIG. 12 is a perspective view of the sheath and stent assembly of FIG. 11 associated with a rapid-exchange delivery catheter.
FIG. 12a is a cross-sectional view of the sheath and rapid-exchange delivery catheter of FIG. 12.

The delivery sheath 28 of FIG. 11 is particularly suited for use with rapid-exchange catheters, such as the rapid exchange catheter 94 with dilatation balloon 95 depicted in FIG. 12. Examples of so-called rapid exchange catheters are shown and described in U.S. Pat. No. 5,180,368 (Garrison), U.S. Pat. No. 5,458,613 (Gharibadeh et al.), and U.S. Pat. No. 5,496,346 (Horzewski et al.), which are incorporated herein by reference.

When used with a rapid-exchange catheter 94, the delivery sheath 28 can be easily removed from and introduced into the patient without necessitating removal of the catheter 94. An additional advantage of the delivery sheath 28 with the mandrel 88 is that the user can maintain a grasp on a catheter proximal portion 96 while removing or inserting the delivery sheath 28. The mandrel may be specifically configured to present a surface that can lie smoothly against the catheter. For example, FIG. 12a shows a mandrel 88 having a curved inner surface 89 configured to lie smoothly against a substantially tubular catheter 94.

The delivery sheath 28 may be placed around the catheter 94 prior to introduction of the catheter 94 into the patient, and the catheter 94 and sheath 28 assembly introduced into the patient in a single step. Alternatively, the delivery sheath 28 may be slidably introduced over the catheter 94 after the catheter 94 is in place in the patient. Such introduction of the delivery sheath over the catheter can be facilitated by having a catheter whose proximal portion 96 has a diameter small enough to pass through the sheath distal portion 34 and short pushable section 92, or with a catheter having a detachable proximal hub.

During introduction of the delivery sheath 28 over the rapid-exchange catheter 94, such as that shown in FIG. 12, the sheath distal portion 34 and short pushable section 92 slide over the rapid exchange catheter 94 and guidewire 26, with the mandrel 88 spaced some distance away from the catheter proximal portion 96 so that the mandrel 88 does not interfere with a user's grasp on the catheter proximal portion 96.

During removal of the delivery sheath 28, the sheath distal portion 34 and short pushable section 92 slide over the rapid exchange catheter 94 and guidewire 26. Toward the catheter proximal portion 96, the mandrel 88 can be pulled laterally away from the catheter 94, thereby allowing the user to retain a firm hold on the catheter proximal portion 96. When the sheath 28 is entirely removed from within the patient, removal of the sheath distal portion 34 and short pushable section 92 from the catheter can be completed by slitting the sides of the sheath distal portion 34 and short pushable section 92. Alternatively, the sheath distal portion 34 and short pushable section 92 may be slid off the catheter proximal portion 96, especially where the catheter proximal portion 96 has a sufficiently small diameter to pass through the sheath distal portion 34 and the short pushable section 92, or where the catheter is equipped with a detachable proximal hub.

Figure 13:
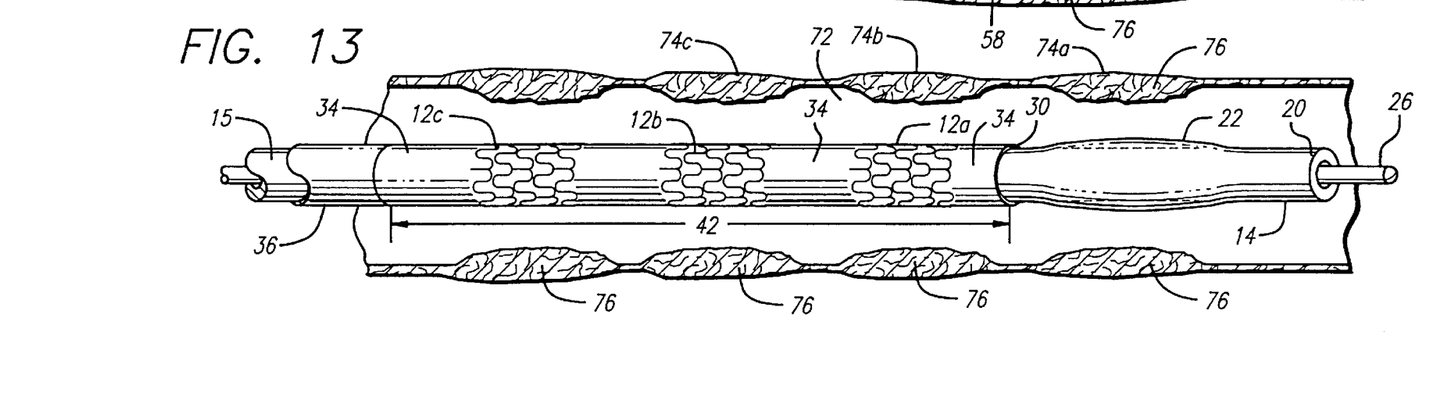
FIG. 13 is a perspective view of a sheath and stent assembly having multiple stents according to the present invention.

FIGS. 1 and 6–12 show a preferred embodiment whereby a single stent 12 is mounted on the sheath 28. However, as shown in FIG. 13, another embodiment involves multiple stents 12a–c mounted on sheath 28. Thus, a single sheath 28 may be used to deploy multiple stents 12a–c in a body lumen during a single procedure, without the need for either the sheath 28 or catheter to be removed from the body lumen until the procedure is completed. In one method, the locations 74a, 74b, 74c to be treated may all be dilated by the dilatation balloon 22 prior to deployment of any of the stents 12. After all locations to be treated have been dilated, the deflated dilatation balloon 22 is positioned at the location 74a where the first stent 12a is to be deployed. The sheath 28 is slidably advanced over the catheter until the first stent 12a is positioned over the deflated dilatation balloon 22. Then the dilatation balloon is expanded, thereby deploying the first stent 12a. The dilatation balloon is then deflated and repositioned at the location 74b where the second stent 12b is to be deployed. The sheath is again slidably advanced over the catheter until the second stent 12b is positioned over the deflated dilatation balloon 22. The dilatation balloon is expanded again to deploy the second stent 12b, and the procedure is repeated for any further stents.

In another method, dilation of selected treatment sights 74a–c may occur just prior to deployment of each stent, so that the first site 74a is dilated prior to deployment of the first stent 12a, the second site 74b is dilated after deployment of the first stent 12a but before the deployment of the second stent 12b, etc.

The stents 12 are preferably spaced apart a distance that allows the dilatation balloon 22 to expand a stent 12 without inadvertently causing full or partial expansion of adjacent stents.

In FIG. 13, the sheath is shown with three stents 12. However, any number of stents 12 may be used, with the length 42 of the sheath distal portion 34 selected to accommodate the particular size and number of stents.

The invention may also be used in procedures where dilation of the body lumen and stent deployment comprise a single step. In such a procedure, the body lumen is not dilated prior to stent deployment. Instead, the outward expansion of the stent during deployment dilates the body lumen.

The distal portion 34 and proximal portion 36 of the sheath 28 may be preformed at the point of manufacture. However, the sheath distal portion 34 may be a separate assembly that is attached to the proximal portion 36 by the user, such as a physician, just prior to or during a procedure. Thus, a physician or other user could select from a variety of stents and sheath distal portions, with the selection of stents and sheath distal portions dependent on the particular application.

Figure 14:
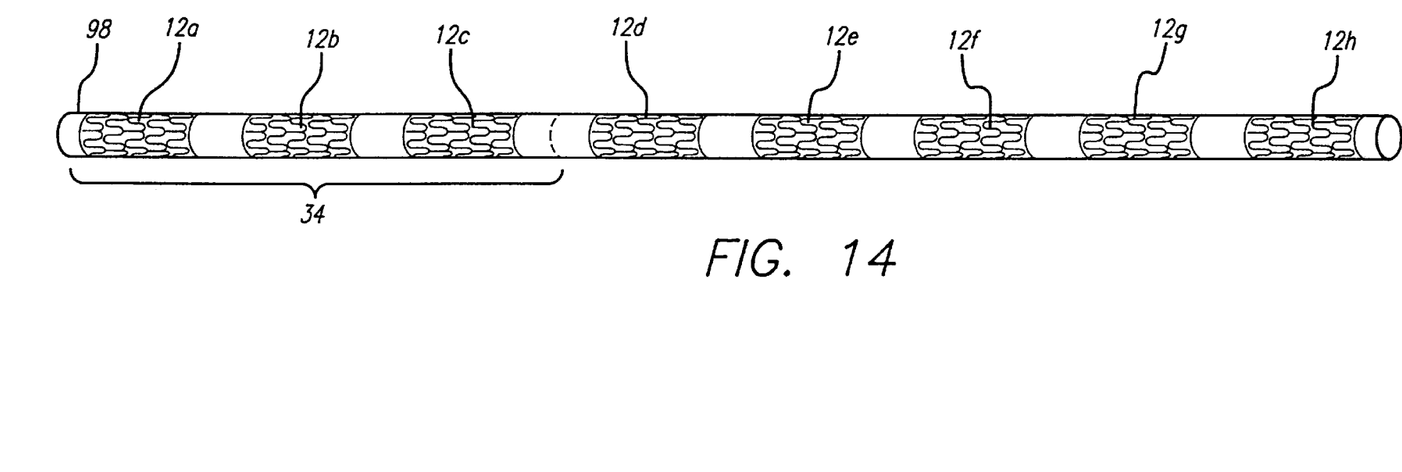
FIG. 14 is a perspective view of a section of sheath distal portion material bearing multiple stents.

The user could also be allowed to customize the length of the sheath distal portion as well as the number of stents located thereon. For example, a user could be provided with a section of sheath distal portion material 98 bearing multiple stents 12, as shown in FIG. 14. The user could then select the length of sheath distal portion and the number of stents desired for a particular procedure, and cut from the length of material 98 a sheath distal portion of the desired length and bearing the selected number of stents. For example, if the user desired three stents, the user could cut a sheath distal portion 34 bearing stents 12a–12c. The user could then secure the "customized" sheath distal portion 34 to a sheath proximal portion to form a completed sheath. The stents 12 are spaced apart by a minimum distance in the range of about 4 mm to 10 mm which allows a user to cut the sheath into separate stent-bearing sections. The spacing also allows the user to deploy a stent without inadvertently deploying adjacent stents with the tapered portion of the expandable balloon.

Figure 15A:
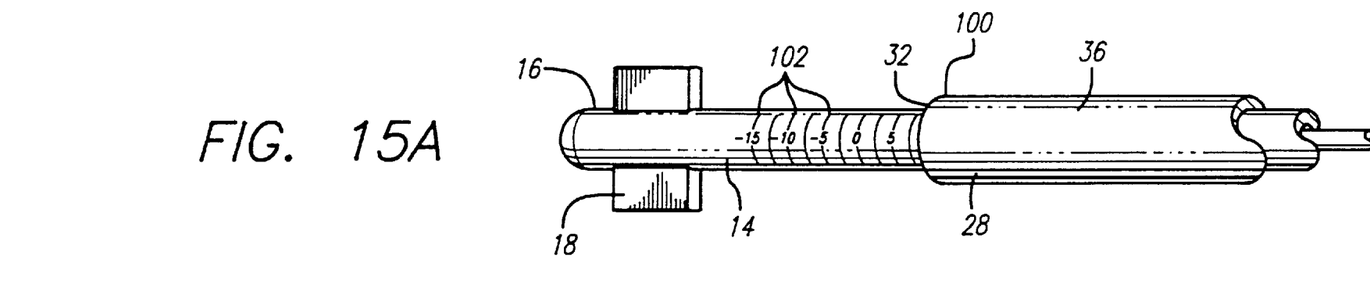
FIG. 15a is a perspective view of a proximal portion of a delivery catheter and sheath assembly having indicia to indicate the position of the distal portion of the sheath relative to the expandable member.
Figure 15B:
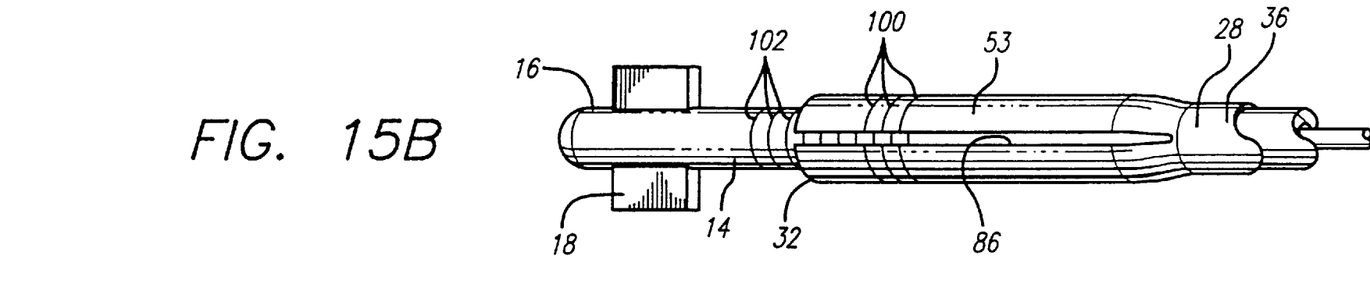
FIG. 15b is a perspective view of a proximal portion of a delivery catheter and sheath assembly according to an alternative embodiment of the invention, wherein the sheath and delivery catheter have indicia to indicate the position of the distal portion of the sheath relative to the expandable member.

FIG. 15a shows another aspect of a preferred embodiment of the invention, whereby the proximal end 32 of the sheath 28 and the proximal end 16 of the catheter 14 have indicia 100, 102 to indicate the position of the sheath 28 relative to the catheter 14, and/or the position of the stent(s) with respect to the dilatation balloon. In the embodiment shown, the catheter 14 has various indicia 102, including numbers and lines, and the sheath indicia 100 simply consists of the sheath proximal end 32. Alignment of the sheath proximal end 32 with the catheter indicia 102 show the position of the stent with respect to the dilatation balloon. For example, in the embodiment of FIG. 15a, alignment of the sheath proximal end 32 with the number "−15" on the catheter may indicate that the longitudinal (i.e., proximal-to-distal) center of the stent is 15 mm proximal of the longitudinal center of the dilatation balloon.

In further embodiments, the sheath indicia 100 may comprise more than merely the sheath proximal end 32. For example, in the embodiment shown in FIG. 15b, a proximal section, such as a handle portion 53, of the sheath 28 may have a slot 86 (or may have view holes or be substantially transparent) and have indicia 100, such as lines or other markings, that can be aligned with corresponding indicia 102 on the catheter 14. In such an embodiment, the slot 86 (or view holes or transparent portion) of the handle 53 allows the catheter indicia 102 to be viewed through the sheath 28.

Figure 15C:
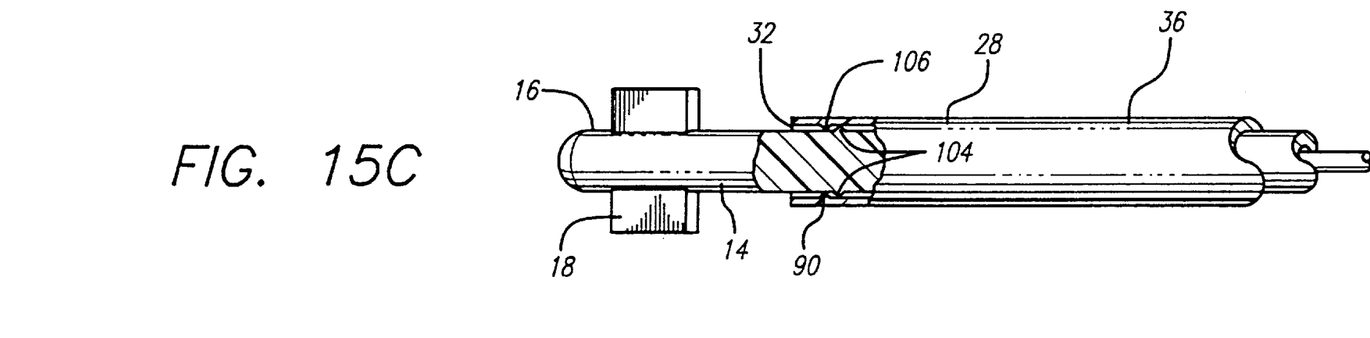
FIG. 15c is a perspective view of a proximal portion of a delivery catheter and sheath assembly according to an alternative embodiment of the invention, wherein the sheath and delivery catheter have indicia to indicate the position of the distal portion of the sheath relative to the expandable member.

In a further embodiment shown in FIG. 15c, the catheter indicia 102 may comprise a disruption 104 in the surface of the catheter 14, and the sheath indicia 100 may comprise a corresponding disruption 106 in the surface of the sheath 28. Alignment of the sheath disruption 106 and catheter disruption 104 cause physical contact therebetween. Such physical contact may be sufficient for a user whose hand is sliding the sheath to detect, by feel, the contact between the sheath disruption 106 and the catheter disruption 104. The physical contact may also be sufficient to resist and/or prevent further longitudinal movement of the sheath over the catheter.

The sheath indicia 100 may further comprise indicia describing characteristics of the particular sheath and/or the stent or stents secured thereto, such as the type and number of stents, etc.

The disclosed embodiments have described the sheath and stent assembly being used with a catheter having an inflatable balloon for deployment of the stent. However, the invention is not limited to the use of expandable balloons. Other expandable devices for lumen dilation and stent deployment are also compatible with the invention.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. A stent deployment system for deploying one or more stents within a body lumen, the system comprising:

a catheter having a shaft with an outer surface, a proximal end, and a distal end including an expandable member;

a substantially tubular sheath having a proximal end and a distal end, a stiff proximal portion located proximally to a less stiff distal portion only, an outer surface, and a lumen therethrough defining an inner surface, the sheath configured for slidable movement over the catheter shaft;

a substantially tubular stent having a delivery configuration and a deployed configuration, the stent being removably attached in the delivery configuration over the distal portion of the sheath and alternately disposed overlying the expandable member and proximal to the expandable member; and a handle disposed at the proximal portion.

2. The system of claim 1, wherein the distal portion of the sheath is formed from a flexible, expandable polymeric material.

3. The system of claim 2, wherein the proximal portion of the sheath is formed from a polymeric material that provides sufficient stiffness to the sheath to allow relative axial movement of the distal portion of the sheath over the catheter in response to axial movement of the proximal end of the sheath over the catheter.

4. The system of claim 3, further comprising a substantially longitudinal slit in the proximal portion of the sheath.

5. The system of claim 1, wherein the catheter has catheter positioning indicia and the sheath has sheath positioning indicia, the catheter positioning indicia and sheath positioning indicia being positioned such that alignment of the sheath positioning indicia with the catheter positioning indicia positions the stent at a desired longitudinal position adjacent to the catheter distal end.

6. The system of claim 5, wherein the catheter positioning indicia includes a visible marker on the catheter, and the sheath positioning indicia includes the proximal end of the sheath.

7. The system of claim 5, wherein the catheter positioning indicia comprises a physical disruption in the outer surface of the catheter, and the sheath positioning indicia comprises a physical disruption in the inner surface of the sheath, wherein alignment of the catheter positioning indicia with the sheath positioning indicia results in physical contact between the catheter positioning indicia and sheath positioning indicia, said contact resisting slidable movement in at least one direction between the catheter and sheath.

8. The system of claim 1, wherein the sheath has a length of at least 50 cm.

9. An apparatus for delivering one or more stents to a desired position within a body lumen, the apparatus comprising:

a catheter having a shaft;

a substantially tubular sheath having a proximal end and a distal end, a stiff proximal portion located proximally to a less stiff distal portion only, an outer surface, and an inner lumen passing therethrough that defines an inner surface passing the length of the sheath, the tubular sheath having sufficient rigidity to be pushable to slidably move the sheath over the catheter shaft;

at least one substantially tubular stent having a delivery configuration and a deployed configuration, the stent being removably attached in the delivery configuration over the distal portion of the sheath; and a handle disposed at the proximal portion.

10. The apparatus of claim 9, wherein the proximal portion of the sheath is formed from a polymeric material that provides sufficient stiffness to the sheath to allow relative axial movement of the distal portion of the sheath over the catheter in response to axial movement of the proximal end of the sheath over the catheter.

11. The apparatus of claim 10, wherein the inner lumen is configured for a catheter shaft having an expandable member to slidably move therewithin, and the distal portion of the sheath is formed from a flexible, expandable polymeric material.

12. The apparatus of claim 10, further comprising a substantially longitudinal slit in the proximal portion of the sheath.

13. The apparatus of claim 9, wherein the sheath includes two or more of said substantially tubular stents, said stents positioned on the distal portion of the sheath.

14. The apparatus of claim 9, wherein the handle includes a slot, said slot configured to receive a catheter shaft therewithin.

15. The apparatus of claim 9, wherein the proximal portion of the sheath includes indicia that describe features of the apparatus.

16. The apparatus of claim 9, wherein the tubular sheath has a length of at least 50 cm.

17. A method for deploying one or more stents in a body lumen, the method comprising the steps of:
   a) positioning a first stent about a flexible distal end portion of a tubular sheath having sufficient rigidity to be pushable to slidably move the sheath over a catheter shaft. having positioning indicia at the distal end portion and a handle at a stiff proximal end portion located proximally to the flexible distal end portion only, the first stent being configured in a delivery configuration;
   b) slidably pushing the tubular sheath over a catheter shaft having positioning indicia;
   c) introducing the catheter shaft into the body lumen;
   d) introducing the tubular sheath into the body lumen;
   e) positioning the first stent at a first desired location within the body lumen; and
   f) deploying the first stent at the first desired location, wherein said first stent assumes a deployed configuration.

18. The method of claim 17, wherein step (a) is performed prior to step (b).

19. The method of claim 17, wherein steps (c) and (d) are performed as a single step.

20. The method of claim 17, wherein the catheter includes an expandable member, and wherein step (c) comprises the further step of:
   g) positioning the expandable member at the first desired position within the body lumen.

21. The method of claim 20, wherein the sheath has a distal end portion formed from a flexible, expandable material, and wherein step (e) occurs after step (g), and wherein step (e) comprises the further step of:
   h) sliding the sheath over the catheter shaft until the first stent is positioned over the expandable member.

22. The method of claim 21, comprising, prior to step (h), the further step of:
   i) dilating the body lumen with the expandable member.

23. The method of claim 17, wherein step (a) comprises the additional step of:
   j) positioning one or more additional stents about a distal end portion of the tubular sheath, each additional stent being configured in a delivery configuration.

24. The method of claim 23, comprising the further steps of:
   k) positioning the additional stents at one or more additional desired locations within the body lumen; and
   l) deploying the additional stents at the additional desired locations, wherein each additional stent assumes a deployed configuration.

25. The method of claim 24, comprising, after steps (k) and (l) are performed, the further steps of:
   m) removing the tubular sheath from the body lumen; and
   n) removing the catheter from the body lumen.

26. The method of claim 25, wherein the tubular sheath includes a slit in the sheath proximal portion, and step (m) includes the step of peeling the sheath away from the catheter.

27. The method of claim 17, wherein the positioning step (e) includes indicia on the catheter shaft and indicia on the tubular sheath, the method further comprising moving the tubular sheath relative to the catheter shaft and aligning the indicia on the tubular sheath with the indicia on the catheter shaft, thereby positioning the stent over an expandable member near a distal end of the catheter shaft.

28. An apparatus for delivering a stent to a desired position within a body lumen, the apparatus comprising:
   a catheter having a shaft with positioning indicia at a distal end;
   a substantially tubular sheath having a stiff proximal portion located proximal to a less stiff distal portion only, an outer surface, and an inner lumen passing therethrough that defines an inner surface passing the length of the sheath, the tubular sheath having sufficient rigidity to be pushable to slidably move the sheath over the catheter shaft and including positioning indicia at the distal end;
   a mandrel having a proximal end and a distal end, wherein the mandrel distal end is attached to the sheath; and
   a handle disposed at the proximal end of the sheath.

29. The apparatus of claim 28, further comprising at least one substantially tubular stent having a delivery configuration and a deployed configuration, the stent being removably attached in the delivery configuration over the sheath.

30. The apparatus of claim 29, wherein the mandrel is formed from a polymeric material that provides sufficient stiffness to the mandrel to allow relative axial movement of the mandrel distal end alongside the catheter in response to movement of the mandrel proximal end.

31. The apparatus of claim 30, wherein the sheath inner lumen is configured for a catheter shaft having an expandable member to slidably move therewithin, and the distal portion of the sheath is formed from a flexible, expandable polymeric material.

32. The apparatus of claim 31, wherein the mandrel is secured to a proximal portion of the sheath, and said proximal portion of the sheath is formed from a polymeric material that provides sufficient stiffness to the sheath to allow relative axial movement of the sheath over the catheter in response to movement of the mandrel proximal end.

33. An apparatus for delivering a plurality of stents to a desired position within a body lumen, the apparatus comprising:
   a catheter having a shaft;
   a substantially tubular sheath having a stiff proximal portion located proximal to a less stiff distal portion only, an outer surface, and an inner lumen passing therethrough that defines an inner surface passing the length of the sheath, the tubular sheath having sufficient rigidity to be pushable to slidably move the sheath over the catheter shaft;
   the plurality of substantially tubular stents, each stent having a delivery configuration and a deployed configuration, the stents being removably attached end to end in the delivery configuration over the sheath at the distal portion; and
   a handle disposed at the proximal end.

34. The apparatus of claim 33, wherein the sheath is formed from a flexible, expandable material.

* * * * *

UNITED STATES PATENT AND TRADEMARK OFFICE
CERTIFICATE OF CORRECTION

PATENT NO. : 6,143,016
DATED : Nov. 7, 2000
INVENTOR(S) : Jeffrey C. Bleam, et al.

It is certified that error appears in the above-identified patent and that said Letters Patent is hereby corrected as shown below:

Column 13, line 20, claim 17, change "a catheter", to
    read --the catheter--.

Column 14, line 39, claim 32, change "a proximal", to
    read --the proximal--.

Signed and Sealed this

Twenty-ninth Day of May, 2001

Attest:

NICHOLAS P. GODICI

Attesting Officer    Acting Director of the United States Patent and Trademark Office